US00PP14241P29

(12) United States Plant Patent
Van Rijssen

(10) Patent No.: US PP14,241 P2
(45) Date of Patent: Oct. 14, 2003

(54) SUTERA PLANT NAMED 'SUTTIPP'

(50) Latin Name: *Sutera cordata*
Varietal Denomination: Suttipp

(76) Inventor: Carel Reinier Van Rijssen, Molengraaf 4, 4133 CM Vianen (NL)

( * ) Notice: Subject to any disclaimer, the term of this patent is extended or adjusted under 35 U.S.C. 154(b) by 0 days.

(21) Appl. No.: 10/163,737

(22) Filed: Jun. 5, 2002

(51) Int. Cl.[7] ..... A01H 5/00
(52) U.S. Cl. ..... Plt./263
(58) Field of Search ..... Plt./263

(56) References Cited

U.S. PATENT DOCUMENTS

PP12,026 P2 * 7/2001 Theobald ..... Plt./263
PP12,682 P2 * 6/2002 Polman ..... Plt./263
PP12,689 P2 * 6/2002 Churchus ..... Plt./263

* cited by examiner

*Primary Examiner*—Bruce R. Campell
*Assistant Examiner*—Susan B. McCormick

(57) ABSTRACT

A new cultivar of Sutera plant named 'Suttipp' that is characterized by medium green leaves, white flowers and a ball-shaped habit. In combination these traits set 'Suttipp' apart from all other existing varieties of Sutera known to the inventor.

3 Drawing Sheets

Genus: Sutera.
Species: *cordata.*
Denomination: Suttipp.

BACKGROUND OF THE INVENTION

The present invention relates to a new and distinct cultivar of Sutera known botanically as *Sutera cordata* and referred to hereinafter by the culivar name 'Suttipp'. 'Suttipp' is a hybrid plant grown for use as an ornamental container plant and hanging basket.

The new cultivar 'Suttipp' resulted from a formal breeding program in which the criteria was to produce new Sutera plants that produce larger flowers than existing varieties. 'Suttipp' was bred by crossing the female parent Sutera 'P08' (not patented) with the male parent Sutera 'SF27' (not patented). 'Suttipp' is distinquishable from its female parent Sutera 'P08' (not patented) by having larger flowers and from its male parent Sutera 'SF27' (not patented) by having larger flowers. The induced cross was conducted in July 1997 by the inventor in a cultivated area of Naaldwijk, The Netherlands. 'Suttipp' was selected by the inventor in April 1998 in Naaldwijk, The Netherlands. Selection was based on the ball-shaped growth habit and medium to large sized flowers.

'Suttipp' is characterized by a ball-shaped growth habit, compact internodes, white flowers and green leaves. The closest comparison plants are Sutera 'Blizzard' (U.S. Plant Pat. No. 10,966) and Sutera 'White Showers' (not patented). 'Suttipp' is distinguishable from 'Blizzard' by its pattern of initially growing upright and later growing prostrate, its compact habit, leaves that are darker green in color, larger and more lustrous and flowers that are brighter white in color. 'Suttipp' is distinguishable from 'White Showers' by foliage that is conspicuously toothed and flowers that are 2–3 mm. larger than the flowers of 'White Showers'.

The first asexual reproduction of 'Suttipp' was conducted by the inventor in a cultivated area of Naaldwijk, The Netherlands in September 1998. The method used for asexual propagation was cuttings taken from the shoots. The characteristics of the new cultivar have been determined one hundred percent stable and are reproduced true to type in successive generations.

SUMMARY OF THE INVENTION

The following traits have been repeatedly observed and represent the characteristics of the new Sutera cultivar 'Suttipp'. These traits in combination distinguish 'Suttipp' from all other commercial varieties known to the inventor. 'Suttipp' has not been tested under all possible conditions and phenotypic differences may be observed with variations in environmental, climatic and cultural conditions.

1. Sutera 'Suttipp' exhibits a ball-shaped growth habit.
2. Sutera 'Suttipp' exhibits medium sized mid-green lustrous foliage.
3. Sutera 'Suttipp' exhibits medium to large white flowers with fused petals and a campanulate tube.
4. Sutera 'Suttipp' is 50–80 cm. in width and 20 cm. in height at maturity.
5. Sutera 'Suttipp' is propagated by cuttings taken from the shoots.
6. Sutera 'Suttipp' is an ornamental suitable for containers and hanging baskets.

BRIEF DESCRIPTION OF THE DRAWINGS

The accompanying drawings illustrate the distinguishing traits of the new cultivar 'Suttipp'. The drawing on sheet 1 illustrates the entire plant in bloom from a side perspective. The drawing on sheet 2 is a close-up view of the flowers and leaves. The drawing on sheet 3 illustrates a typical Sutera flower being held adjacent to a flower on a Sutera 'Suttipp' plant. The drawings were made using conventional techniques and although colors may appear different from actual colors due to light reflectance they are as accurate as possible by conventional photography.

BOTANICAL DESCRIPTION OF THE PLANT

The following is a detailed description of the Sutera cultivar named 'Suttipp'. Data was collected in Arroyo Grande, Calif. from plants grown in 2-litre containers out-of-doors in full sun. The plants were approximately 18-months-old at the time. The color determinations are in accordance with The 2001 R.H.S. Color Chart of The Royal Horticultural Society, London, England, except where general color terms of ordinary dictionary significance are used. Growing conditions, diseases and pests are similar to that of other Sutera. There are no growing problems known to the inventor.

Botanical classification: Sutera 'Suttipp'.
Species: *cordata.*
Commercial classification: Perennial herb.
Use: Ornamental for hanging baskets and containers.
Recommended container size: 1-litre.
Cultural requirements: Performs best in full sunlight with moderate to regular water and well-drained rich compost soil.
Parentage: Sutera 'Suttipp' is a hybrid resulting from the induced hybridization of the following parent plants:
*Female parent.*—Sutera 'P08'.
*Male parent.*—Sutera 'SF27'.
Plant description:
*Bloom period.*—Summer to fall.
*Diseases and pests.*—Normal tolerance of pests and disease.
*Plant habit.*—Broad, spreading habit.
*Shape.*—Flattened ball shape.
*Vigor.*—Vigorous.
*Height.*—12 cm. in height.
*Width.*—35 cm. in width.
*Root system.*—Dense, fine and freely branching.
*Propagation.*—Propagation is accomplished by taking cuttings from the shoots.
*Time to develop roots.*—14 days at temperature of 20° Centigrade is needed for initial cuttings to develop roots in summer and 21 days at temperature of 15° Centigrade in winter.
*Crop time.*—2 months at 20° Centigrade are needed to produce a finished liner in summer and 3 months at 15° Centigrade to produce a finished liner in winter.
*Growing recommendations.*—Pinching required.
Stem:
*Stem color.*—139A.
*Quantity of lateral branches.*—50 lateral branches.
*Lateral branch length.*—15 cm. in length.
*Lateral branch diameter.*—1.5 mm. in width.
*Stem surface.*—Pubescent.
*Internode length.*—2 cm.
*Branching habit.*—Freely branching.
*Other stem characteristics.*—Slightly fragrant.
*Stipules, spines, thorns.*—None.
Foliage:
*Type.*—Evergreen.
*Compound or single.*—Single.
*Quantity of leaves per lateral branch.*—14 leaves.
*Arrangement.*—Opposite.
*Shape.*—Orbicular.
*Division.*—Simple.
*Apex.*—Rounded.
*Base.*—Attenuate.
*Venation pattern.*—Laciniate.
*Vein color* (*abaxial surface*).—137C.
*Vein color* (*adaxial surface*).—137A.
*Leaf length.*—2 cm. in length.
*Leaf width.*—2.1 cm. in width.
*Leaf margins.*—Serrate.
*Texture.*—Dull and smooth.
*Attachment.*—Petiolate.
*Petiole dimensions.*—10 mm. in length and 1 mm. in width.
*Petiole color.*—137A.
*Leaf surfaces* (*adaxial and abaxial*).—Pubescent.
*Young leaf color* (*adaxial surface*).—143A.
*Young leaf color* (*abaxial surface*).—137D.
*Mature leaf color* (*adaxial surface*).—137A.
*Mature leaf color* (*abaxial surface*).—137C.
*Durability of foliage to stress.*—High.
*Other foliage characteristics.*—Slightly convexed.
Flowers:
*Arrangement.*—In pairs and axillary.
*Form.*—Single.
*Flower shape.*—Salverform.
*Flowering habit.*—Continuously.
*Quantity of flowers per lateral stem.*—10 flowers.
*Quantity of flower buds per lateral stem.*—10 buds.
*Quantity of flowers and buds per plant.*—500 flowers and buds per plant.
*Natural flowering season.*—Summer through fall.
*Time to flower or response time.*—8–10 weeks.
*Rate of flower opening.*—20% open at once.
*Fragrance.*—None.
*Flower longevity on plant.*—One week.
*Persistent or self-cleaning.*—Persistent.
*Aspect.*—Facing upward.
*Flower diameter.*—1.5 cm. in diameter.
*Flower height.*—1 cm. in height.
*Petal arrangement.*—Rotate.
*Petal apprearance.*—Dull.
*Number of petals.*—Five.
*Petal fused or unfused.*—Tube fused.
*Shape of petal.*—Rounded.
*Petal margin.*—Entire.
*Petal apex.*—Rounded.
*Petal length.*—6 mm. in length.
*Petal width.*—5 mm. in width.
*Petal color.*—155D.
*Color of corolla* (*throat*).—14B on the inside surface and 14C on the outside surface.
*Bud dimensions.*—9 mm. in length and 3 mm. in width.
*Bud shape.*—Obovate.
*Bud color.*—149D.
*Calyx color.*—143A.
*Calyx dimensions.*—10 mm. in length and 15 mm. in width.
*Sepal.*—Five in number.
*Sepal arrangement.*—Rotate.
*Sepal dimensions.*—10 mm. in length and 3 mm. in width.
*Sepal margin.*—Entire.
*Sepal apex.*—Acute.
*Sepal surface.*—Pubescent.
*Sepal color* (*adaxial surface*).—143A.
*Sepal color* (*abaxial surface*).—137B.
*Peduncle dimensions.*—4 mm. in length and 2 mm in width.
*Peduncle color.*—137D.
Reproductive organs:
*Stamens.*—Four in number.
*Anther color.*—14A.
*Anther dimensions.*—1 mm. in width and 1.20 mm. in length.

*Anther shape.*—Oval and dorsifixed.
*Pollen color.*—14A.
*Amount of pollen.*—Low.
*Pistil.*—One.
*Pistil dimensions.*—10 mm. in length and 1 mm. in width.
*Style dimensions.*—9 mm. in length and 1 mm. in width.
*Style color.*—144B.
*Stigma shape.*—Club-shaped.
*Stigma color.*—144B.
*Ovary color.*—137B.

Seed production: Sutera 'Suttipp' does not produce seed.

What is claimed is:

1. A new and distinct cultivar of Sutera plant named 'Suttipp' as described and illustrated herein.

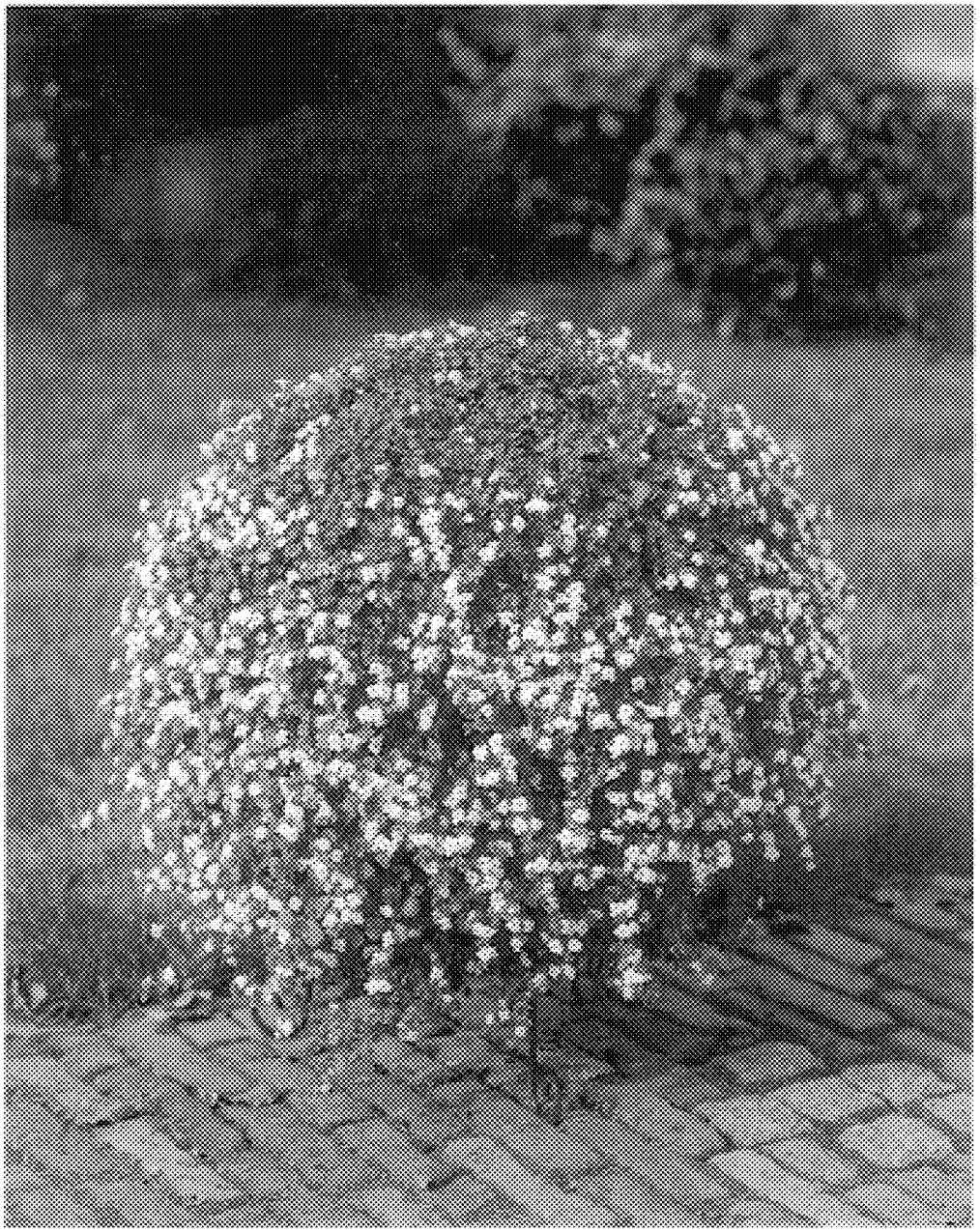

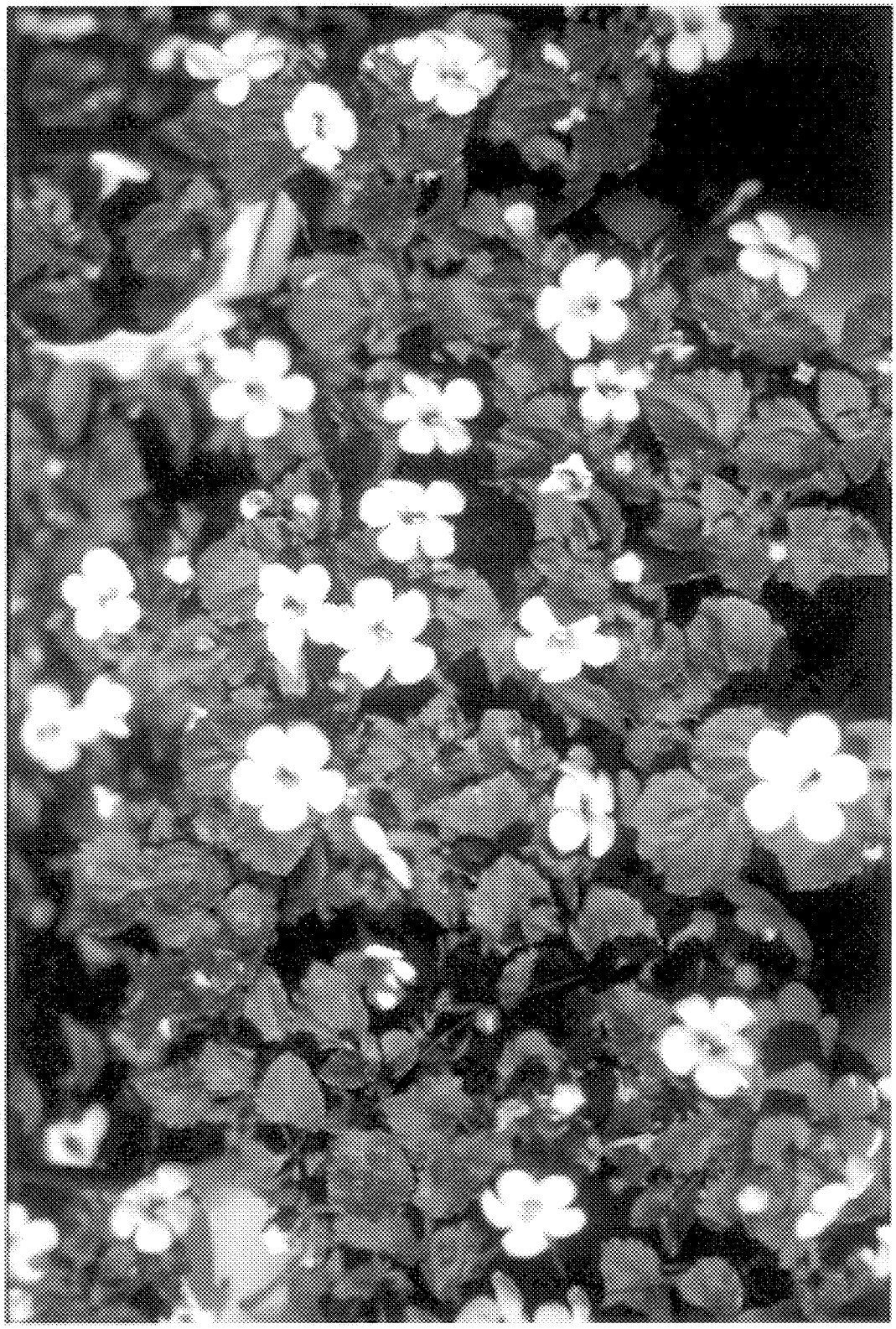

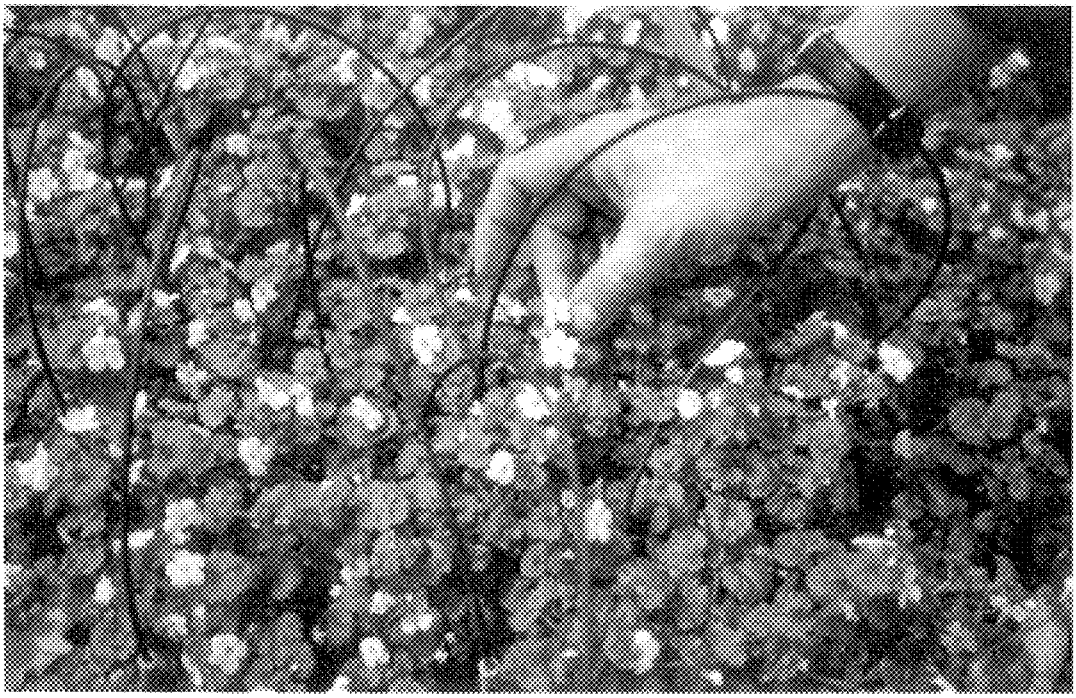

* * * * *